United States Patent [19] [11] Patent Number: 5,831,128
Beller et al. [45] Date of Patent: Nov. 3, 1998

[54] SYNTHESIS OF AROMATIC AMINES FROM CHLOROAMATICS

[75] Inventors: Matthias Beller, Ismaning; Thomas Riermeier, München; Claus Peter Reisinger, Graiching; Wolfgang Anton Herrmann, Freising; Holger Geissler, Mainz, all of Germany

[73] Assignee: Hoechst Aktiengesellschaft, Germany

[21] Appl. No.: 984,554

[22] Filed: Dec. 3, 1997

[30] Foreign Application Priority Data

Dec. 4, 1996 [DE] Germany ............... 196 50 213.6

[51] Int. Cl.$^6$ .................................. C07C 209/10
[52] U.S. Cl. .................. 564/405; 564/407; 544/178; 546/192
[58] Field of Search .................. 564/405, 407; 544/178; 546/192

[56] References Cited

U.S. PATENT DOCUMENTS 5,576,460  11/1996  Buchwald et al. .................. 564/386
5,723,669   3/1998  Goodbrand et al. .

OTHER PUBLICATIONS

Reddy et al., "Palladium–Catalyzed Amination of Aryl Chlorides", Tetrahadron Letters, vol. 38, No. 27, pp. 4807–4810 (1997).

Louie et. al., "Palladium–Catalyzed Synthesis of Arylamines from Aryl Halides. Mechanistic Studies Lead to Coupling in the Absence of Tin Reagents", Tetrahedron Letters, vol. 36, No. 21, pp. 3609–3612 (1995).

Primary Examiner—Brian M. Burn
Attorney, Agent, or Firm—Connolly & Hutz

[57] ABSTRACT

The present invention relates to a process for the preparation of aromatic amines of the formula (I)

$$Ar-NR^1R^2 \quad (I)$$

in which Ar is

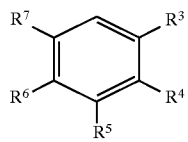

or

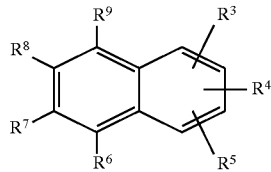

and $R^3$ to $R^9$ independently of one another are hydrogen, $C_1$–$C_8$-alkyl, alkoxy-($C_1$–$C_8$), acyloxy-($C_1$–$C_8$), OAr, Ar, fluorine, chlorine, bromine, iodine, OH, $NO_2$, CN, $CO_2H$, CHO, $SO_3H$, $SO_2R$, SOR, $NH_2$, NH-alkyl-($C_1$–$C_{12}$), N-alkyl$_2$-($C_1$–$C_{12}$), NHCO-alkyl-($C_1$–$C_{12}$), CO-alkyl-($C_1$–$C_{12}$), NHCHO, COAr, $CO_2$Ar, $CF_3$, $CONH_2$, $CHCHCO_2R$, POAr$_2$, PO-alkyl$_2$-($C_1$–$C_{12}$), 5-ring heteroaryl, 6-ring heteroaryl, Si-alkyl$_3$-($C_1$–$C_{12}$), where R=alkyl($C_1$–$C_8$), aryl($C_5$–$C_{10}$) and $R^1$ and $R^2$ independently of one another are hydrogen, $C_1$–$C_{12}$-alkyl, Ar as defined above, 5-ring heteroaryl, 6-ring heteroaryl, by reacting chloroaromatics of the formula II $$Ar-Cl \quad (II)$$

with ammonia or primary or secondary amines of the formula III $$R^1R^2NH \quad (III)$$

in which Ar and $R^1$ and $R^2$ are as defined above, which comprises reacting the starting materials in the presence of a palladium catalyst, a strong base and a halide cocatalyst in an inert solvent at temperatures of 80°–200° C.

12 Claims, No Drawings

SYNTHESIS OF AROMATIC AMINES FROM CHLOROAMATICS

The present invention relates to a process for the preparation of aromatic amines from the corresponding chloroaromatics, in particular to a process for the preparation of substituted anilines, using a palladium catalyst.

Aromatic amines, particularly substituted anilines, are of great industrial significance as intermediates for dyes, fine chemicals, pharmaceuticals and agricultural products.

Substituted anilines are prepared industrially inter alia by nitration of a corresponding aromatic compound and subsequent hydrogenation. Since nitration takes place under drastic reaction conditions, many complex substituted anilines can only be synthesized inadequately in this way or not at all.

An alternative method of preparing anilines is the ammonolysis of phenols and chlorobenzene (K. Weissermel, J.-J. Arpe, Industrielle Organische Chemie [Industrial Organic Chemistry], 3rd edition, p. 396 et seq.). Because of the process method, such as the drastic reaction conditions required (temperatures>180°–420° C.; pressures of 60–200 bar), these reactions are likewise not suitable for the preparation of substituted anilines.

Novel palladium-catalyzed aminations of iodo- and bromoaromatics which lead to substituted anilines were recently described in A. S. Guram, R. A. Rennels, S. L. Buchwald, Angew. Chem. 1995, 107, 1459 and J. Lonie, J. F. Hartwig, Tetrahedron Lett., 1995, 36, 3609. These reactions are carried out under comparatively mild reaction conditions and can therefore also be used for variously substituted anilines. The iodo- and bromoaromatics used as starting compounds are, however, expensive and not readily available.

It is, therefore, of great industrial interest to develop a process in which substituted aromatic amines, in particular also complex substituted anilines, can be prepared under mild reaction conditions from generally available starting compounds which are also cheap.

According to the invention this object is achieved by a process for the preparation of aromatic amines of the formula (I)

$$Ar-NR^1R^2 \qquad (I)$$

in which Ar is

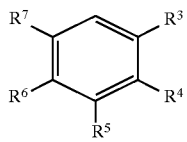

or

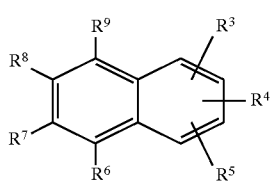

and $R^3$ to $R^9$ independently of one another are hydrogen, $C_1$–$C_8$-alkyl, alkoxy-($C_1$–$C_8$), acyloxy-($C_1$–$C_8$), OAr, Ar, fluorine, chlorine, bromine, iodine, OH, $NO_2$, CN, $CO_2H$, CHO, $SO_3H$, $SO_2R$, SOR, $NH_2$, NH-alkyl-($C_1$–$C_{12}$), N-alkyl$_2$-($C_1$–$C_{12}$), NHCO-alkyl-($C_1$–$C_{12}$), CO-alkyl-($C_1$–$C_{12}$), NHCHO, COAr, $CO_2$Ar, $CF_3$, $CONH_2$, CHCHCO$_2$R, POAr$_2$, PO-alkyl$_2$-($C_1$–$C_{12}$), 5-ring heteroaryl, 6-ring heteroaryl, Si-alkyl$_3$-($C_1$–$C_{12}$) where R=alkyl($C_1$–$C_8$), aryl($C_5$–$C_{10}$) and $R^1$ and $R^2$ independently of one another are hydrogen, $C_1$–$C_{12}$-alkyl, Ar as defined above, 5-ring heteroaryl, 6-ring heteroaryl, by reacting chloroaromatics of the formula II $$Ar-Cl \qquad (II)$$

with ammonia or primary or secondary amines of the formula III $$R^1R^2NH \qquad (III)$$

in which Ar and $R^1$ and $R^2$ are as defined above, which comprises reacting the starting materials in the presence of a palladium catalyst, a strong base and a halide cocatalyst in an inert solvent at temperatures of 80°–200° C.

Examples of compounds which can be easily obtained using the process according to the invention are arylpiperazines, arylpiperidines, aryldibutylamines, arylmorpholines, arylphenylmethylamines, aryldiethylamines, arylphenylamines, where aryl is preferably phenyl, methoxyphenyl, trifluoromethylphenyl, acetylphenyl, fluorophenyl, difluorophenyl, methylphenyl, pyridyl and naphthyl.

For the process according to the invention, the palladium catalyst preferably contains at least one phosphorus-containing ligand.

The palladium catalyst may already contain the at least one phosphorus-containing ligand, but the palladium catalyst containing the phosphorus-containing ligands can also be formed from catalyst precursors.

The catalyst precursors used in this connection are preferably palladacycles and/or palladium(0) or -(II) compounds in the presence of phosphorus-containing ligands such as phosphine ligands.

Suitable examples of palladacycles are trans-di($\mu$-aceto) bis[o(di-o-tolylphosphino)benzyl]dipalladium(II) and the corresponding bromo- or chloro-bridged compounds or compounds, in which the tolyl radical may be replaced by mesityl or t-butyl radicals.

Palladium compounds which can be used are Pd(0)-complex compounds and Pd(II) compounds. Suitable examples are palladium acetates, halides, nitrates, carbonates, ketonates, acetylacetonates, nitrilopalladium halides, olefinpalladium halides, allylpalladium halides and palladium biscarboxylates. Specific examples are Pd(OAc)$_2$, Pd(acac)$_2$, (CH$_3$CN)$_2$Pd(NO$_2$)Cl, (C$_{10}$H$_8$N$_2$)PdCl$_2$, Pd$_2$(dba)$_3$ and PdCl$_2$.

The palladium compound can also be produced in situ, for example from palladium(II) acetate or palladium(II) chloride by adding a customary reducing agent.

The phosphorus-containing ligands are preferably mono- or bidentate phosphine ligands.

Examples of compounds which are suitable as phosphine ligands are triphenylphosphine, tricyclohexylphosphine, bisdiphenylphosphinoethane, bisdiphenylphosphinopropane, bisdiphenylphosphinobutane, tri-n-butylphosphine, triisopropylphosphine, bisdiphenylphosphinobenzene, bisdiphenylphosphinobinaphthyl, diphenylphosphinopyridine, it being possible for the phenyl radicals to be substituted or, when required, replaced by one or more $C_1$ to $C_{12}$-alkyl or $C_3$ to $C_{10}$-cycloalkyl groups. A particularly preferred ligand is tri-o-tolylphosphine.

The ligands are used inter alia in a P/Pd ratio of 8:1 to 1:1. The catalyst is generally used in quantities of from 0.0001 mol-% to 10 mol-%, preferably from 0.001 mol-% to 5 mol-% (based on the chloroaromatics).

In the process of the invention, amines react with chloroaromatics over a palladium catalyst in the presence of a strong base whose $pK_a$ value is preferably greater than 10. Examples of bases which can be used are strongly basic alkali metal and alkaline earth metal derivatives such as alkali metal alkoxides and alkaline earth metal alkoxides, alkali metal and alkaline earth metal amides, and also butyllithium, phenyllithium, etc. Preferred bases are alkali metal and alkaline earth metal alkoxides such as sodium tert-butoxide, potassium tert-butoxide, lithium tert-butoxide, sodium phenoxide, potassium phenoxide and potassium carbonate, sodium hexamethyldisilazide and lithium hexamethyldisilazide.

The base is preferably used in a quantity of 0.5–5 equivalents, in particular 1–3 equivalents and very particularly preferably 1.2–2 equivalents, based on the chloroaromatics.

The solvents used are usually inert organic solvents. Preference is given to aromatic hydrocarbons such as toluene, xylenes, anisole, tetralin and aliphatic ethers such as tetrahydrofuran, dimethoxyethane, dioxane, tetrahydropropane and formaldehyde acetals.

The chloroaromatics are reacted at temperatures of from 80° to 200° C., preferably at 100°–180° C. and particularly preferably at 120°–180° C.

The halide cocatalyst can be alkali metal and/or alkaline earth metal bromides, chlorides or iodides. Ammonium and phosphonium bromides, chlorides or iodides can also be used. Preferred halides are the corresponding bromides such as lithium bromide, sodium bromide, potassium bromide and tetraalkylammonium bromides. The halide cocatalyst is used in quantities of 0.1–100 mol-%, preferably 3–50 mol-%, based on the chloroaromatics. As a liquid salt, it can also serve as a solvent.

The process according to the invention is particularly suitable for the reaction of primary aromatic amines and secondary aliphatic and aromatic amines. The amine is usually added in virtually stoichiometric quantities or in excess, based on the chloroaromatics. The quantity of amine is preferably 1 to 3 equivalents, in particular 1.2 to 2 equivalents.

Electron withdrawing substituents on the chloroaromatic also have a particularly favorable effect on reactions. Examples of suitable electron withdrawing substituents are $NO_2$, R—(CO)—, $CF_3$—, F, CN, where R can be a branched or linear alkyl radical.

The reaction is preferably carried out under a usual protective gas such as $N_2$, He or Ar.

The substituted arylamines are generally formed in the process according to the invention in good to very good yields of 50–99%. Byproducts in the form of dehalogenation products, which can easily be removed, are sometimes observed.

As an extension of the intermolecular coupling, simple intramolecular aminations can also be carried out.

Starting compounds for this can be 2-arylethylamines, 3-arylpropylamines, 4-arylbutylamines, 2-arylpropylamines, where aryl is as defined above.

The examples below serve merely to illustrate the process without limiting it thereto.

EXAMPLES

General working instructions (GWI): 20 mmol of chloroaromatic, 24 mmol of amine, 28 mmol of KOtBu, 4 mmol of lithium bromide and 1 mol-% of palladium catalyst are suspended in 100 ml of toluene and the mixture is poured into a pressure tube under protective gas and stirred in an oil bath at 140° C. A brown coloration of the yellow reaction mixture is observed. After 24 h, the mixture is cooled to room temperature, filtered off from the salts and washed with diethyl ether. The solvents are removed on a rotary evaporator. Column chromatography (hexane/ethyl acetate: 50/1) gives the desired product.

Example 1

In accordance with the GWI, 2.0 mmol of 4-chlorobenzotrifluoride, 2.4 mmol of piperidine, 2.8 mmol of potassium tert-butoxide, 0.4 mmol of lithium bromide, 1.0 mol-% (9.4 mg) of palladacycle ((trans-di($\mu$-aceto)-bis[o[di-o-tolylphosphino)benzyl]dipalladium(II) in 10 ml of toluene are reacted. 4-Trifluoromethylphenylpiperidine and 3-trifluoromethylphenylpiperidine in the ratio 6:1 are obtained in 65% yield.

Example 2

2.0 mmol of 4-chlorobenzotrifluoride, 2.4 mmol of morpholine, 2.8 mmol of potassium tert-butoxide, 0.4 mmol of lithium bromide, 1.0 mol-% (9.4 mg) of palladacycle (trans-di($\mu$-aceto)-bis[o[di-o-tolylphosphino)benzyl] dipalladium(II) in 10 ml of toluene are reacted according to the GWI to give 4-trifluoromethylphenylmorpholine and 3-trifluoromethylphenylmorpholine in the ratio 5:1 in 62% yield.

Example 3

2.0 mmol of 4-chlorobenzotrifluoride, 2.4 mmol of di-n-butylamine, 2.8 mmol of potassium tert-butoxide, 0.4 mmol of lithium bromide, 1.0 mol-% (9.4 mg) of palladacycle (trans-di($\mu$-aceto)-bis[o[di-o-tolylphosphino)benzyl] dipalladium (II) in 10 ml of toluene are reacted according to the GWI to give 4-trifluoromethylphenyl-di-n-butylamine and 3-trifluoromethylphenyl-di-n-butylamine in the ratio 7:1 in 58% yield.

Example 4

2.0 mmol of 4-chlorofluorobenzene, 2.4 mmol of piperidine, 2.8 mmol of potassium tert-butoxide, 0.4 mmol of lithium bromide, 1.0 mol-% (9.4 mg) of palladacycle (trans-di($\mu$-aceto)-bis[o[di-o-tolylphosphino)benzyl] dipalladium(II) in 10 ml of toluene are reacted according to the GWI to give 4-fluorophenylpiperidine and 3-fluorophenylpiperidine in the ratio 2:1 in 75% yield.

We claim:

1. A process for the preparation of aromatic amines of the formula (I)

in which Ar is

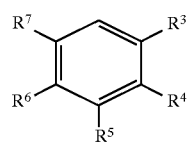

or

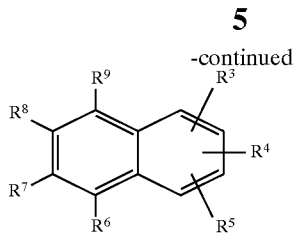

and $R^3$ to $R^9$ independently of one another are hydrogen, $C_1$–$C_8$-alkyl, alkoxy-($C_1$–$C_8$), acyloxy-($C_1$–$C_8$), OAr', Ar', fluorine, chlorine, bromine, iodine, OH, $NO_2$, CN, $CO_2H$, CHO, $SO_3H$, $SO_2R$, SOR, $NH_2$, NH-alkyl-($C_1$–$C_{12}$), N-alkyl$_2$-($C_1$–$C_{12}$), NHCO-alkyl-($C_1$–$C_{12}$), CO-alkyl-($C_1$–$C_{12}$), NHCHO, COAr', $CO_2$Ar', $CF_3$, $CONH_2$, $CHCHCO_2R$, POAr'$_2$, PO-alkyl$_2$-($C_1$–$C_{12}$), 5-ring heteroaryl, 6-ring heteroaryl or Si-alkyl$_3$-($C_1$–$C_{12}$) where R is alkyl($C_1$–$C_8$) or aryl($C_5$–$C_{10}$),
and where Ar' is

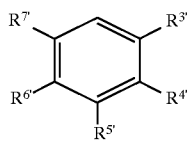

or

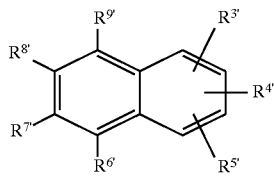

and $R^{3'}$ to $R^{9'}$ independently of one another are hydrogen, $C_1$–$C_8$-alkyl, alkoxy-($C_1$–$C_8$), acyloxy-($C_1$–$C_8$), fluorine, chlorine, bromine, iodine, OH, $NO_2$, CN, $CO_2H$, CHO, $SO_3H$, $SO_2R$, SOR, $NH_2$, NH-alkyl-($C_1$–$C_{12}$), N-alkyl$_2$-($C_1$–$C_{12}$), NHCO-alkyl-($C_1$–$C_{12}$), CO-alkyl-($C_1$–$C_{12}$), NHCHO, $CF_3$, $CONH_2$, $CHCHCO_2R$, PO-alkyl$_2$-($C_1$–$C_{12}$), 5-ring heteroaryl, 6-ring heteroaryl or Si-alkyl$_3$-($C_1$–$C_{12}$) where R is alkyl($C_1$–$C_8$) or aryl($C_5$–$C_{10}$) and $R^1$ and $R^2$ independently of one another are hydrogen, $C_1$–$C_{12}$-alkyl, Ar as defined above, 5-ring heteroaryl, 6-ring heteroaryl, by reacting chloroaromatics of the formula II $$Ar\text{—}Cl \qquad (II)$$

with ammonia or primary or secondary amines of the formula III $$R^1R^2NH \qquad (III)$$

in which Ar and $R^1$ and $R^2$ are as defined above, which comprises reacting the starting materials in the presence of a palladium catalyst, a strong base and a halide cocatalyst in an inert solvent.

2. The process as claimed in claim 1, wherein the palladium catalyst contains at least one phosphorus-containing ligand.

3. The process as claimed in claim 2, wherein said at least one phosphorus-containing ligand is triphenylphosphine, tricyclohexylphosphine, bisdiphenylphosphinoethane, bisdiphenylphosphinopropane, bisdiphenylphosphinobutane, tri-n-butylphosphine, triisopropylphosphine, bisdiphenylphosphinobenzene, bisdiphenylphosphinobinaphthyl, diphenylphosphinopyridine or tri-o-tolylphosphine.

4. The process as claimed in claim 1, wherein said palladium catalyst is prepared in situ from a palladium compound and at least one phosphorus-containing ligand.

5. The process as claimed in claim 4, wherein the palladium compound is palladacycles, Pd(0) complex compounds or Pd(II) compounds.

6. The process as claimed in claim 5, wherein the palladium compound is $Pd(OAc)_2$, $Pd(aca)_2$, $(CH_3CN)_2Pd(NO_2)Cl$, $(C_{10}H_8N_2)PdCl_2$, $Pd(dba)_3$ or $PdCl_2$.

7. The process as claimed in claim 1, wherein said strong base is an alkali metal base, alkaline earth metal base or a mixture thereof.

8. The process as claimed in claim 7, wherein said strong base is an alkali metal alkoxides, alkaline earth metal alkoxides, alkali metal amides, alkaline earth metal amides, butyllithium, phenyllithium, potassium carbonate, sodium hexamethyidisilazide or lithium hexamethyldisilazide or mixtures thereof.

9. The process as claimed in claim 1, wherein the halide cocatalyst is an alkali metal bromide, alkali metal chloride, alkali metal iodide, alkaline earth metal bromide, alkaline earth chloride, alkaline earth iodide, ammonium bromide, ammonium chloride, ammonium iodide, phosphonium bromide, phosphonium chloride or phosphonium iodide or mixtrures thereof.

10. The process as claimed in claim 1, wherein the reaction is carried out at a temperature in the range from 80° C. to 200° C.

11. The process as claimed in claim 2, wherein the reaction is carried out at a temperature in the range from 100° to 180° C.

12. The process as claimed in claim 5, wherein the reaction is carried out at a temperature in the range from 120° to 180° C.

* * * * *